United States Patent
Ha et al.

(10) Patent No.: US 10,842,814 B2
(45) Date of Patent: Nov. 24, 2020

(54) USE OF LOW DOSE ARSENIC FOR PRESERVING GENOMIC INTEGRITY

(71) Applicants: Board of Regents of the University of Texas System, Austin, TX (US); Baylor College of Medicine, Houston, TX (US)

(72) Inventors: Chul Soo Ha, Houston, TX (US); Zhi-Min Yuan, Chestnut Hill, MA (US); Hang Su, San Antonio, TX (US); Edward Paul Hasty, San Antonio, TX (US); Alison A. Bertuch, Houston, TX (US); Maria Monica Gramatges, Houston, TX (US); Gregory P. Swanson, Austin, TX (US)

(73) Assignees: Board of Regents of the University of Texas System, Austin, TX (US); Baylor College of Medicine, Houston, TX (US)

(*) Notice: Subject to any disclaimer, the term of this patent is extended or adjusted under 35 U.S.C. 154(b) by 0 days.

(21) Appl. No.: 16/326,049

(22) PCT Filed: Aug. 16, 2017

(86) PCT No.: PCT/US2017/047098
§ 371 (c)(1),
(2) Date: Feb. 15, 2019

(87) PCT Pub. No.: WO2018/035200
PCT Pub. Date: Feb. 22, 2018

(65) Prior Publication Data
US 2019/0183929 A1   Jun. 20, 2019

Related U.S. Application Data

(60) Provisional application No. 62/375,657, filed on Aug. 16, 2016.

(51) Int. Cl.
A61K 33/36    (2006.01)
A61P 35/00    (2006.01)
A61P 43/00    (2006.01)
A61K 9/00     (2006.01)

(52) U.S. Cl.
CPC ............ *A61K 33/36* (2013.01); *A61K 9/0019* (2013.01); *A61P 35/00* (2018.01); *A61P 43/00* (2018.01)

(58) Field of Classification Search
CPC ...................................... A61K 33/36
USPC ............................................. 424/623
See application file for complete search history.

(56) References Cited

U.S. PATENT DOCUMENTS

2012/0294955 A1   11/2012   Yuan

OTHER PUBLICATIONS

International Search Report and the Written Opinion of the International Searching Authority corresponding to International Patent Application No. PCT/US2017/047098 (10 pages) (dated Nov. 6, 2017).
Shim et al. "Crosstalk between telomere maintenance and radiation effects: A key player in the process of radiation-induced carcinogenesis" Mutation Research/Reviews in Mutation Research, 760:1-17 (2014).
Extended European Search Report for European Patent Application No. EP17842042.8 (8 pages) (dated Mar. 10, 2020).
Ferrario et al. "Sodium arsenite induces telomerase and telomeres modulation in human cord blood cells 'in vitro'" Toxicology Letters, 180:S102-103 (2008).
Lin et al. "Arsenic trioxide for refractory aplastic anemia" Annals of Hematology, 92:3 (2013).
Prakash et al. "Role of Arsenic Trioxide in the Management of Aplastic Anemia" Indian Journal of Hematology and Blood Transfusion, 33:4 (2017).
Zhang et al. Effects of arsenic on telomerase and telomeres in relation to cell proliferation and apoptosis in human keratinocytes and leukemia cells in vitro Carcinogenesis, 24:11 (2003).
Zhang et al. "Up-regulation of telomere-binding TRF1, TRF2 related to reactive oxygen species induced by As2O3 in MGC-803 cells" European Journal of Pharmacology, 516:1 (2005).

*Primary Examiner* — Raymond J Henley, III
(74) *Attorney, Agent, or Firm* — Myers Bigel, P.A.

(57) ABSTRACT

Methods and compositions are provided for inhibiting, preventing, ameliorating and/or reducing damage to DNA in non-cancerous cells in a subject undergoing chemotherapeutic treatment and/or radiation treatment of cancer cells in the subject, comprising administering to the subject one or more compounds of arsenic in a therapeutically effective amount prior to chemotherapeutic treatment and/or radiation treatment.

6 Claims, 9 Drawing Sheets

USE OF LOW DOSE ARSENIC FOR PRESERVING GENOMIC INTEGRITY

STATEMENT OF PRIORITY

This application is a 35 U.S.C. § 371 national phase application of International Application Serial No. PCT/US2017/047098, filed Aug. 16, 2017, which claims the benefit, under 35 U.S.C. § 119(e), of U.S. Provisional Application No. 62/375,657, filed Aug. 16, 2016, the entire contents of each of which are incorporated by reference herein.

FIELD OF THE INVENTION

The present invention relates to the protection of genomic integrity of non-cancerous cells from chemotherapy and/or radiation therapy, thereby reducing the development of secondary malignancy attributable to chemotherapy and/or radiation therapy and to the treatment of disorders associated with telomere dysfunction.

BACKGROUND OF THE INVENTION

Cancers are a leading cause of death in animals and humans. During the past decades, a combination of chemotherapy and radiation therapy along with surgery has become a standard approach for treatment of cancer patients in the curative as well as in the palliative setting. Though radiation and chemotherapy are successful modalities of cancer therapy, they do not greatly differentiate between cancerous and normal cells. Thus, in the process of killing cancer cells, radiation or chemotherapeutic agents also damage normal tissues leading to systemic toxicity and adverse side effects, which often poses a significant threat to cancer patients. Adverse side effects also greatly limit the maximum allowable dose. Efforts to avoid the toxicity of chemotherapy and radiation therapy have not yielded significant results despite multiple efforts in the past.

The telomere, which is considered a guardian of genomic integrity, gets shorter in normal tissues after treatment or exposure to DNA damaging agents such as chemotherapy and radiation therapy. This shortening contributes to genomic instability, which in turn contributes to development of treatment (or exposure) related malignancy. For example, secondary myelodysplastic syndrome (MDS) and acute myeloid leukemia (AML) are life-threatening late effects of cancer treatment. Damage in DNA of bone marrow cells by radiation and chemotherapy that leads to genomic defects and instability of these cells is thought to contribute to the development of MDS and AML.

The present invention overcomes previous shortcomings in the art by providing methods and compositions to ameliorate DNA damage in noncancerous cells in subjects undergoing radiation therapy or chemotherapy. The present invention also provides methods and compositions to treat disorders associated with telomere dysfunction.

SUMMARY OF THE INVENTION

In one aspect, the present invention provides a method of inhibiting, preventing, ameliorating and/or reducing genomic damage to non-cancerous cells in a subject undergoing radiation treatment and/or chemotherapeutic treatment of cancer cells in the subject comprising: a) administering to the subject, in need of radiation treatment and/or chemotherapeutic treatment for the treatment of cancer, one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

In an additional aspect, the present invention provides a method of inhibiting, preventing, ameliorating and/or reducing telomere shortening in non-cancerous cells in a subject undergoing radiation treatment and/or chemotherapeutic treatment of cancer cells in the subject comprising: a) administering to the subject, in need of radiation treatment and/or chemotherapeutic treatment for the treatment of cancer, one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

A further aspect of this invention is a method of preventing and/or reducing the risk of developing a secondary or subsequent malignancy in a subject undergoing radiation treatment and/or chemotherapeutic treatment of cancer cells present in the subject, comprising: a) administering to the subject one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

Additionally provided herein is a method of treating, ameliorating and/or preventing a disease or disorder associated with telomere dysfunction in a subject in need thereof, comprising administering to the subject an effective amount of one or more compounds of arsenic.

Figure 1:
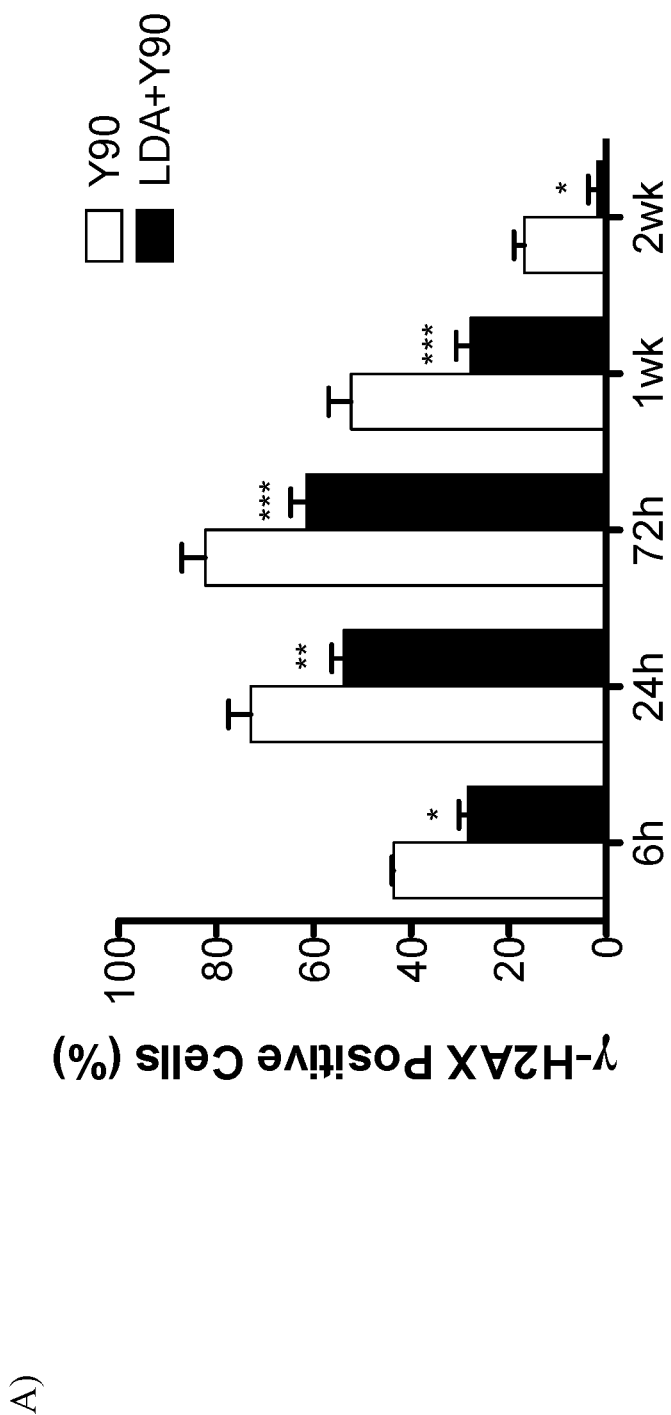
FIG. 1. γ-H2AX and TUNEL staining of bone marrow sections at different time points after Y-90 ibritumomab tiuxetan treatment. Balb/c mice were pretreated with or without low-dose arsenic (LDA) for three days, followed by administration of 200 µCi Y-90 ibritumomab tiuxetan (Y90) via tail vein injection. At the indicated time points, mice were sacrificed by cervical decapitation and bone marrows were harvested for staining. (A) Quantification of γ-H2AX positive cells. (B) Quantification of TUNEL positive cells in bone marrow sections. *$P<0.05$, $P<0.01$, *$P<0.001$.
Figure 1:
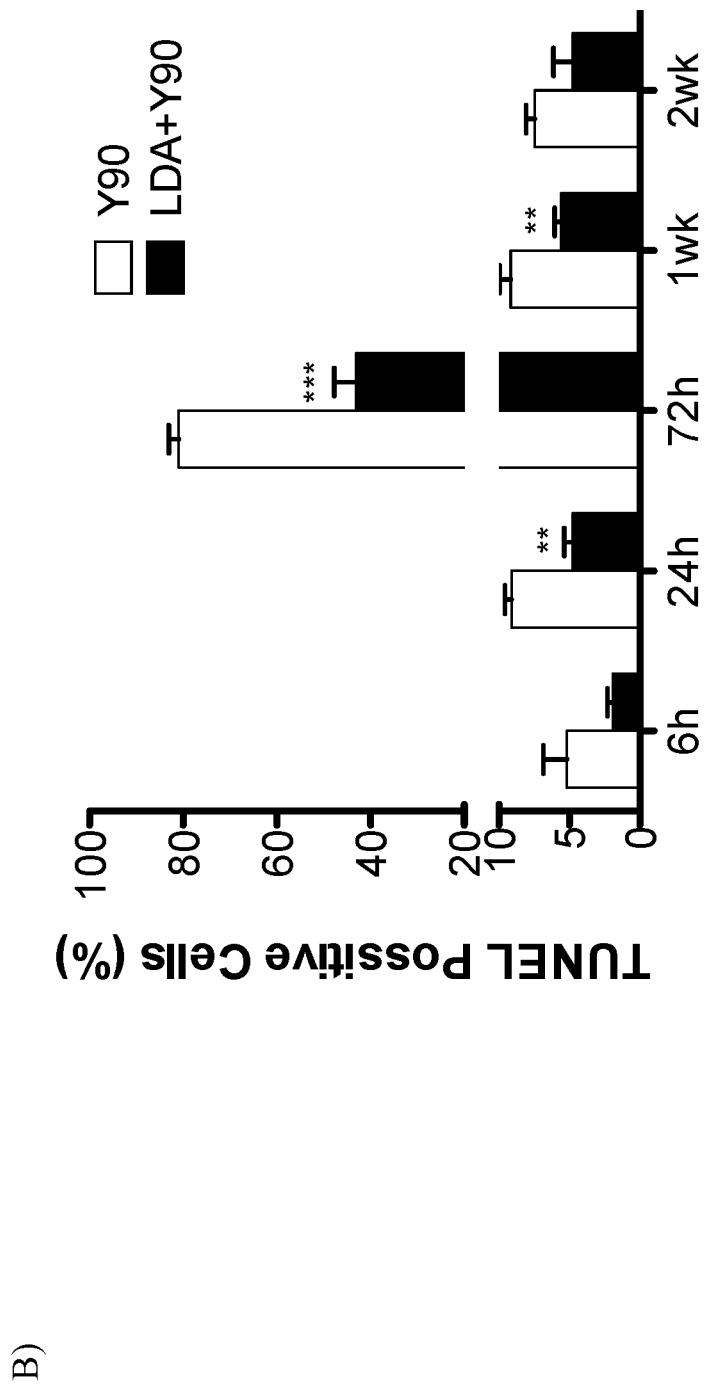

Advantages of the present invention will become apparent to those skilled in the art with the benefit of the following detailed description of embodiments and upon reference to the accompanying drawings described herein.

DETAILED DESCRIPTION OF THE INVENTION

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

As used herein, the singular forms "a," "an" and "the" are intended to include the plural forms as well, unless the context clearly indicates otherwise.

As used herein, the term "and/or" includes any and all combinations of one or more of the associated listed items.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to a composition of the present invention would "materially alter" the composition if it increases or decreases the composition's durability by at least 20%.

As used herein, the terms "enhance" and "increase" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "decrease" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

The present invention is directed, in part, to the unexpected discovery that LDA protects genomic integrity in non-cancerous cell. Thus, in one embodiment, the present invention provides a method of inhibiting, preventing, or reducing genomic damage to non-cancerous cells in a subject undergoing radiation treatment and/or chemotherapeutic treatment of cancer cells in the subject comprising: a) administering to the subject, in need of radiation treatment and/or chemotherapeutic treatment for the treatment of cancer, one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

As used herein, genomic damage refers to any damage that breaches the integrity of the genetic material in a cell.

In another embodiment, the present invention provides a method of inhibiting, preventing, or reducing telomere shortening in non-cancerous cells in a subject as a result of radiation treatment and/or chemotherapeutic treatment of cancer cells in the subject comprising: a) administering to the subject, in need of radiation treatment and/or chemotherapeutic treatment for the treatment of cancer, one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

As used herein, telomere shortening refers to the loss or reduction of the length of telomeric DNA in a cell as a consequence of administration of radiation and/or a chemotherapeutic agent.

The present invention also provides a method of preventing or reducing the risk of developing a subsequent malignancy in a subject undergoing radiation treatment and/or chemotherapeutic treatment of cancer cells present in the subject, comprising: a) administering to the subject one or more compounds of arsenic in a protective amount of from about 1 µg/kg/day to about 125 µg/kg/day, wherein the one or more compounds of arsenic are administered to the subject at least one day prior to administration of radiation and/or one or more chemotherapeutic agents to the subject; and b) administering to the subject radiation and/or one or more chemotherapeutic agents subsequent to administration of the one or more compounds of arsenic.

As used herein, the terms "secondary malignancy," "treatment-related secondary malignancy" or "subsequent malignancy" refers to a malignancy in a subject that is attributable to the toxic effects of radiation and/or a chemotherapeutic agent administered to the subject to treat a primary malignancy.

Also as used herein, a "subject undergoing radiation treatment and/or chemotherapeutic treatment" is a subject that has previously received such treatment, is currently receiving such treatment and/or will be receiving such treatment, consistent with the context in which this phrase is used herein.

A further aspect of this invention is the unexpected discovery that LDA treatment may have a beneficial and/or therapeutic effect on a subject that has, or is suspected of having, or is at risk of having, a disease or disorder associated with telomere dysfunction. Thus, in an additional embodiment, the present invention provides a method of treating and/or preventing a disease or disorder associated with telomere dysfunction in a subject (e.g., a subject in need thereof), comprising administering to the subject an effective amount of one or more compounds of arsenic. As used herein, a "subject in need thereof" refers to a subject that has, is suspected of having or is at risk of having, a telomere-mediated disease, a telomere syndrome, a telomeropathy, a genetic defect in telomere replication and extension, abnormal telomere biology and/or a telomere biology disorder.

Nonlimiting examples of a disease or disorder associated with telomere dysfunction include dyskeratosis congenita, aplastic anemia, idiopathic pulmonary fibrosis, Hoyeraal-Hreidarsson syndrome, Revesz syndrome, Coats plus syndrome, and any other syndrome in which a subject's leukocytes have telomere lengths below the first percentile for age-matched controls.

As used herein the terms "administration," "administering," or the like, when used in the context of providing a composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered by a parenteral, subcutaneous, intravenous, intrathecal, intracoronary, rectal, intramuscular, intraperitoneal, transdermal, and/or buccal route of delivery. Alternatively, or concurrently, administration may be by an oral, nasal, pulmonary, or gastric route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "cancer" as used herein is defined as a tissue of uncontrolled growth or proliferation of cells, such as a malignant tumor. In a specific embodiment, the tumor leads to local invasion and metastasis.

The term "chemotherapeutic agent" as used herein is defined as a drug, toxin, compound, molecule, composition or biological entity or agent that is used or can be used as treatment for cancer.

The term "cytotoxic agent" as used herein is defined as a drug, toxin, compound, molecule, composition or biological entity or agent that is used or can be used to kill a cell. In an embodiment, the cell is a cancer cell.

The term "DNA-damaging agent" as used herein refers to a drug, toxin, compound, molecule, composition or biological entity or agent that damages the structure and/or inhibits the function of a nucleic acid molecule. The damage may be of any kind to the nucleic acid, for example, to break one or both strands of a DNA double helix molecule or to cause mutation of one or more nucleotides.

The term "drug" as used herein is defined as a medicament or medicine that is used for the therapeutic treatment of a medical condition, disorder or disease. The drug may be used in combination with another drug and/or type of therapy and in an embodiment of this invention, the drug is effective for the treatment of cancer.

The term "pharmaceutically or pharmacologically acceptable" as used herein refers to molecular entities and compositions that do not produce adverse, allergic, or other untoward reactions when administered to an animal or a human.

The term "pharmaceutically acceptable carrier" as used herein includes any and all solvents, dispersion media, coatings, antibacterial and antifungal agents, isotonic and absorption delaying agents and the like.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art.

A pharmaceutical composition may be provided as sustained-release or timed-release formulations. Such formulations may release a bolus of a compound from the formulation at a desired time, or may ensure a relatively constant amount of the compound present in the dosage is released over a given period of time.

Terms such as "sustained release," "controlled release," or "timed release" and the like are widely used in the pharmaceutical arts and are readily understood by a practitioner of ordinary skill in the art.

Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the term "subject" generally refers to a mammal, and in particular embodiments, refers to a human of any age (e.g., fetus, neonate, infant, pediatric, adolescent, adult, geriatric, etc.), race or gender. In one embodiment, the subject who receives the arsenic-containing compound of this invention is one who is undergoing chemotherapy and/or radiation therapy. For example, the subject can be a human subject or an animal for which chemotherapy and/or radiation therapy is considered to be an advantageous treatment. In one embodiment, a subject of this invention can be a subject of any age, race or gender that has, is suspected of having, or is at risk of having a telomere dysfunction or a disease or disorder associated with a telomere dysfunction.

As used herein, the terms "treat," "treatment" and "treating" refer to reversing, alleviating, reducing the severity of and/or inhibiting the progress of a disease or disorder as described herein, or at least one symptom of a disease or disorder as described herein. The treatment need not provide a complete cure and is considered effective if at least one symptom is improved upon or eradicated. Furthermore, the treatment need not provide a permanent improvement of the disease state or medical condition.

As used herein, the terms "prevent," "preventing," and "prevention" (and grammatical variants thereof) refer to avoiding or delaying the onset of a disorder and/or a clinical symptom(s) in a subject relative to what would occur in the absence of the methods of the present invention. In some embodiments, prevention is complete, resulting in the total absence of the disorder and/or clinical symptom(s) (e.g., a total absence of growth of a pathogenic microbial strain).

The terms "in need of treatment," "in need thereof," "who would benefit from such treatment," or the like when used in the context of a subject being administered a pharmacologically active composition, generally refers to a judgment made by an appropriate healthcare provider that a subject requires or will benefit from a specified treatment, therapy or medical intervention. Such judgments may be made based on a variety of factors that are in the realm of expertise of healthcare providers, but include knowledge that the subject is ill, will be ill, or is at risk of becoming ill, as the result of a condition that may be ameliorated or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a subject in need of treatment, including dosage forms, routes of administration, and frequency of dosing, may depend upon the particulars of the condition that is encountered, including the patient and condition being treated, the severity of the condition in a particular subject, the particular compound being employed, the particular route of administration being employed, the frequency of dosing, and the particular formulation being employed. Determination of a therapeutically effective treatment regimen for a subject is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the subject treated and the particular mode of administration.

The term "protective amount" as used herein describes an effective amount of an arsenic-containing compound administered to a subject, simultaneously, separately, and/or sequentially with radiotherapy and/or one or more chemotherapeutic agents, which is sufficient to reduce, prevent or otherwise ameliorate the genomic damage caused by the radiotherapy and/or chemotherapeutic drugs on normal cells.

The term "cancer cell" as used herein is defined as a cell of a malignant mass. In some embodiments, the cell may be located within a tumor, on the surface of a tumor, and/or it may be associated with a tumor.

As used herein the terms "reducing," "inhibiting" and "ameliorating," when used in the context of modulating a pathological or disease state, generally refer to the prevention and/or reduction of at least a portion of the negative consequences of the disease state. When used in the context of a biochemical event or pathway, the term generally refers to a net reduction in the magnitude or activity of said pathway.

It is to be understood the present invention is not limited to particular chemotherapies or radiation therapies, which may, of course, vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like, include the number recited and refer to ranges which can be subsequently broken down into sub-ranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

Most types of cancer may be treated with chemotherapy and/or radiation therapy. LDA is useful for reducing genomic damage associated with chemotherapy or radiation therapy treatment of cancers such as breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer. Various animal models for such cancers are known, which can be used to explore the effectiveness of arsenic, as well as administration and dosing protocols. In some embodiments, the subject receives a protective amount of arsenic followed by a chemotherapeutic agent that is not an arsenic-containing compound.

In an embodiment, a method is provided in which the genomic damage associated with chemotherapy and/or radiation therapy in a subject is inhibited by administering one or more compounds of arsenic to the subject, in conjunction with (e.g., prior to, concomitant with and/or following) the administration of a chemotherapeutic agent and/or radiation to the subject. The one or more compounds of arsenic are administered in an amount that is effective to reduce the genomic damage, but that is in an amount that is much less than an amount that will induce additional tumor formation. In some embodiments, one or more compounds of arsenic are administered prior to the administration of chemotherapy or radiation therapy to the subject. In an embodiment, one or more compounds of arsenic are administered substantially simultaneously, or after, the administration of chemotherapy or radiation therapy to the subject. One or more compounds of arsenic may be administered before, during and after chemotherapy or radiation therapy. The reduction in the severity of post-chemotherapy and post-radiation therapy genomic damages increases the quality of life experienced by subjects undergoing chemotherapy and/or radiotherapy.

An arsenic compound of this invention can be administered at any point in time (e.g., before, during and/or after) near the administration of the treatment (e.g., chemotherapy or radiotherapy) to yield a desired protective effect. In one embodiment, arsenic is administered to a subject prior to administration of the treatment, for example, from 1 to 2 days prior, from 1 to 3 days prior, from 1 to 4 days prior, from 1 to 5 days prior, from 1 to 6 days prior, from 1 to 7 days prior, from 1 to 8 days prior, from 1 to 9 days prior, or from 1 to 10 days prior to the administration of the treatment. In some embodiments, the arsenic is administered to a subject at least 1 day prior, at least 2 days prior, at least 3 days prior, at least 4 days prior, at least 5 days prior, at least 6 days prior, at least 7 days prior, at least 8 days prior, at least 9 days prior or at least 10 days prior to the administration of the treatment. In some embodiments, the arsenic is administered to a subject at least 2 consecutive days prior, at least 3 consecutive days prior, at least 4 consecutive days prior, at least 5 consecutive days prior, at least 6 consecutive days prior, at least 7 consecutive days prior, at least 8 consecutive days prior, at least 9 consecutive days prior or at least 10 consecutive days prior to the administration of the treatment. In one embodiment, arsenic is administered 3 days prior to the administration of the treatment. During this period, administration may occur at least once a day, at least twice a day, at least three times a day, at least four times a day, at least six times a day, etc., or substantially continuously (e.g., by intravenous administration). Administration of the treatment can include any time interval, including hourly, daily, weekly, monthly, yearly, etc., in any combination, as well as in any time interval between these units of time (e.g., biweekly, every other day, etc.).

Typically, an effective amount of an arsenic composition of this invention, sufficient for achieving a protective effect, ranges from about 0.5 µg per kilogram body weight per day to about 500 µg per kilogram body weight per day (e.g., about 0.5, 1.0, 2.0, 3.0, 4.0, 5.0, 6.0, 7.0, 8.0, 9.0, 10, 15, 20, 25, 30, 35, 40, 45, 50, 55, 60, 65, 70, 75, 80, 85, 90, 95, 100, 105, 110, 115, 120, 125, 130, 140, 150, 160, 170, 180, 190, 200, 225, 250, 275, 300, 325, 350, 375, 400, 425, 450, 475 or 500 µg per kilogram body weight per day). In some embodiments, the effective amount ranges from about 1.0 µg per kilogram body weight per day to about 30 µg per kilogram body weight per day. In other embodiments, the effective amount ranges from about 1 to about 125 µg/kg/day, about 5 to about 150 µg/kg/day, about 5 to about 250 µg/kg/day, about 5 to about 300 µg/kg/day, about 5 to about 350 µg/kg/day, about 10 to about 400 µg/kg/day, about 15 to about 450 µg/kg/day, or about 15 to about 500 µg/kg/day. In other embodiments, the effective amount ranges from about 1 to about 30 µg/kg/day, about 5 to about 30 µg/kg/day, about 5 to about 25 µg/kg/day, about 5 to about 20 µg/kg/day, about 10 to about 20 µg/kg/day, or about 15 to about 20 µg/kg/day. In suitable embodiments, the dosage is about 5 µg/kg/day, about 10 µg/kg/day, about 20 µg/kg/day, about 30 µg/kg/day, about 35 µg/kg/day, about 40 µg/kg/day, about 50 µg/kg/day, about 100 µg/kg/day, about 150 µg/kg/day, about 250 µg/kg/day, or about 500 µg/kg/day. In different embodiments, the arsenic compound of this invention can inhibit, reduce, or prevent genomic damage to non-cancerous cells by at least 5%, at least 10%, at least 15%, at least 20%, at least 25%, at least 30%, at least 40%, at least 50%, at least 60%, at least 70%, at least 80%, at least 90% or more, compared to a control cell or a control subject or a population of control subjects that were not administered the arsenic compound.

Examples of compounds of arsenic that may be used according to this invention include, but are not limited to, arsenic (III) oxide (arsenic trioxide, $As_2O_3$), arsenic (V) oxide ($As_2O_5$), arsenic (III) selenide ($As_2Se_3$), arsenic (II) sulfide ($As_2S_2$), arsenic (III) sulfide ($As_2S_3$), arsenic (V) sulfide ($As_2O_5$), arsenic (III) telluride ($As_2Te_3$), sodium arsenate ($Na_2HAsO_4$), sodium arsenite ($NaAsO_2$), potassium arsenate ($KH_2AsO_4$), sodium arsenyl tartrate ($NaC_4H_4AsO_6$), tetraarsenic tetrasulfide ($As_4S_4$) and other derivatives of arsenic.

In some embodiments, the determination of effectiveness of LDA treatment can be made at any time following therapy with a chemotherapy or radiation agent. For example, the determination of effectiveness can be made at 1, 2, 3, 4, 5, 6, 7, 8, 9, 10 or more days after the agent (e.g., chemotherapeutic agent or radiation) is delivered to the subject. A sample of cells can be obtained from the subject for this analysis. In order to compare the result obtained with the cells of the subject to the expected result if no pretreatment with arsenic was made, data can be collected from one or more control subjects, preferably from several subjects, who receive the same or similar chemotherapy or radiation therapy, but who do not receive arsenic. Suitably, the control population is being treated for the same condition, e.g., for the same type of cancer. An amount is a protective amount if any benefit whatsoever is produced compared to the control subject(s) and/or population.

In some embodiments, the effectiveness of LDA treatment of this invention is demonstrated by a reduction in the incidence of treatment-related secondary malignancy. Thus, a determination of effectiveness of the LDA treatment can be made at time intervals of days, weeks, months and/or years following the treatment. Such a determination can be made by screening and/or examining the subject for signs and/or symptoms of treatment-related secondary malignancy according to protocols well known in the art for detecting and diagnosing malignancy.

Radiotherapeutic agents and factors include radiation and waves that induce DNA damage for example, gamma-irradiation, X-rays, UV-irradiation, microwaves, electronic emissions, radioisotopes, and the like. Therapy may be achieved by irradiating the localized tumor site with the above described forms of radiations. It is most likely that all of these factors affect a broad range of damage on DNA; on the precursors of DNA; on the replication and repair ability of DNA, and on the assembly and maintenance of chromosomes.

In some embodiments, the methods of the present invention can be carried out in a subject that is undergoing and/or will undergo external beam radiation therapy, brachytherapy involving insertion of a radioactive source in the body of the subject and/or radiopharmaceutical therapy involving administration of radioactive agent to the subject by, e.g., intravenous administration.

Chemotherapeutic agents include agents that directly cross-link DNA, agents that intercalate into DNA, and agents that lead to chromosomal and mitotic aberrations by affecting nucleic acid synthesis. Examples of chemotherapeutic agents include, but are not limited to doxorubicin, daunorubicin, mitomycin, actinomycin D, bleomycin, cisplatin, etoposide, tumor necrosis factor, taxol, vincristine, vinblastine, carmustine, melphalan, cyclophosphamide, chlorambucil, busulfan, fluorouracil ("5FU") and lomustine. Any of these agents may be used alone, or in combination with other agents, after pre-treatment of the patient with one or more compounds of arsenic.

Agents that directly cross-link nucleic acids, specifically DNA, are envisaged and are shown herein, to eventuate DNA damage leading to a synergistic antineoplastic combination. Agents such as cisplatin and other DNA alkylating agents may be used.

Agents that damage DNA also include compounds that interfere with DNA replication, mitosis, and chromosomal segregation. Examples of these compounds include doxorubicin (also known as adriamycin), etoposide (also known as VP-16), verapamil, podophyllotoxin, and the like. Widely used in clinical setting for the treatment of neoplasms, these compounds are administered through bolus injections intravenously at doses ranging from 25-75 mg/m$^2$ at 21 day intervals for adriamycin, to 35-100 mg/m$^2$ for etoposide intravenously or orally.

Induction of DNA damage is one of the principal modes of action for both radio- and chemotherapies to kill cancer cells. It also potently activates p53. Abundant evidence indicates that DNA damaging anticancer therapy-induced acute toxicity is mainly mediated by p53, which upon activation, induces massive apoptotic cell death in sensitive tissues, including intestinal epithelium, spleen, bone marrow, thymus, tongue, testis and hair follicles, leading to severe pathological consequences. In line with these observations is the finding that cells with defective p53 are resistant to DNA damage-induced apoptosis. Moreover, genetic studies have shown that p53-deficient mice are refractory to toxicity induced by radiation and chemotherapy. The p53-mediated pathological response to chemotherapy and radiation therapy would suggest that suppression of p53 may serve as a potential approach for amelioration of the adverse side effects, allowing patients to tolerate much more aggressive (and so potentially more successful) treatment regimes. However, p53 is one of the most important tumor suppressors, so the potential cancer risk resulting from its inhibition needs to be addressed.

The p53 tumor suppressor is a transcription factor that controls the expression of a number of genes whose products mediate cell cycle arrest, DNA repair, senescence, or apoptosis. The critical role of p53 in prevention of carcinogenesis is supported by its universal inactivation in cancer cells either through mutations affecting the p53 locus directly or through aberration of its normal regulation. Because the DNA damage response pathway and the oncogenic stress pathway converge on p53, it has been thought that both pathways are integral to the tumor suppressor function of p53. Recent genetic studies, however, have provided compelling evidence indicating that the oncogenic stress pathway, rather than the DNA damage pathway, is essential for p53-mediated tumor suppression. Using a genetically engineered mouse model in which p53 status can be reversibly switched in vivo between functional and inactive states, it has been shown that the p53-mediated DNA damage responses are irrelevant to tumor suppression but are responsible for the pathological consequences. Of interest is the finding that delayed p53 restoration until the acute DNA damage response has subsided retains the protection against cancer development and such protection depends on p19ARF. Consistent with the notion that the acute DNA damage response may be dispensable for p53-mediated tumor suppression is a mouse genetic study in which endogenous p53 was replaced by a mutant that cannot be phosphorylated by DNA damage-activated protein kinases (ATM, ATR or Chk2). The knockin mice were incompetent for DNA damage-induced apoptosis yet fully protected from cancer development. These studies together indicate that temporary suppression of p53 activity can significantly reduce DNA damage-induced cytotoxicity without compromising the tumor suppression function, providing a rationale to explore temporary p53 inhibition as an approach of cancer therapy protection.

Arsenic is a naturally occurring metalloid that induces oxidative stress by activating NADPH oxidase activity through a Ras-GTPase-dependent mechanism, which creates an intracellular burst of reactive oxygen. Exposure of human, experimental animals and cultured cells to arsenic is associated with a variety of diverse effects. While arsenic is an established human carcinogen, there has been much controversy about the shape of the arsenic response curve, particularly at low doses. This controversy is further complicated by the fact that the mechanism of arsenic carcinogenesis remains unclear because of a lack of consistent success in inducing cancer in animal models through arsenic exposure. Epidemiological studies that include low dose data also indicate that exposure to arsenic in drinking water at concentrations of less than approximately 60 ppb (0.8 μM) is associated with risks of bladder or lung cancer that are below control values. However, when absorbed at toxic levels, arsenic causes severe health problems, including cancer. For instance, in many regions of Bangladesh, high concentrations of arsenic in drinking water becomes a particular health concern as it has been correlated with increased cancer rates. However, arsenic has also been touted as having beneficial effects on health at lower doses. For instance, from the 18th to early 20th century, an inorganic arsenic preparation known as Fowler's Solution (1% potassium arsenate) was used in the treatment of a variety of diseases including skin cancers, hypertension, and arthritis. Arsenic was even applied to the skin by women to improve their complexion. A concentration-related hierarchy of responses to arsenic has been well documented. For example, in human adult foreskin keratinocytes, arsenite treatment at concentrations at or below 5 µM for 24 hr resulted in induced proliferation that is accompanied with enhanced nuclear factor-κB (NF-κB) and activator protein-1 (AP-1) activity, transcription factors that are known to promote cell proliferation and cell survival. At concentrations of 10 µM or greater, a statistically significant decrease of cell viability was observed. In support of the distinct nature of the cellular effects induced by low and high concentrations of arsenic, a genomic analysis showed that low dose (5 µM, non-cytotoxic) and high dose (50 µM, cytotoxic) affected expression of almost completely non-overlapping subsets of genes, consistent with a qualitative switch from a pro-survival biological response at low doses to a pro-death response at high doses. Together, the available information indicates a biphasic dose response of arsenic; the effects induced by low-dose arsenic are not only different in magnitude from that of high-dose arsenic but also in nature, i.e., cytoprotective versus cytotoxic.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Malignancies such as myelodysplastic syndrome (MDS) and acute myeloid leukemia (AML) have been associated with chemotherapy or radiation exposure that could be in the setting of accident or medical intervention. Genomic instability and inability to repair DNA damage (from an agent such as chemotherapy and radiation) in hematopoietic stem cells have been attributed to the development of MDS and AML. Patients with shorter telomere length after a first cancer occurrence are more likely to develop a second malignancy. Radiation and chemotherapy shorten the telomere length of lymphocytes (obtained from donors' peripheral blood and proliferated with Concanavalin A) and bone marrow mononuclear cells undergo accelerated shortening of telomere length in patients treated with Y-90 ibritumomab tiuxetan, an anti-CD20 antibody conjugated to radioactive yttrium used to treat lymphoma. A potential long-term complication from radioimmunotherapy such as Y-90 ibritumomab tiuxetan has been its contribution to the development of MDS and AML. As the telomere is considered a guardian of genomic stability, shortening of telomere length in hematopoietic stem cells of patients treated with radiation may play a role in the development of MDS and AML.

Activation of p53 is one of the major pathways by which DNA damaging agents such as radiation therapy and chemotherapy cause toxicity in normal tissues and it induces a cascade of events that eventually leads to cell senescence or death. Low dose arsenic trioxide (LDA), by temporarily and reversibly suppressing p53 activation at the time of treatment with radiation or chemotherapy, reduces the normal tissue toxicity without compromising tumor response to treatment. Our in vitro and in vivo studies have shown that pretreatment of untransformed cells with LDA induces concerted p53 suppression and NF-kB activation, which elicit a marked induction of glycolysis. This metabolic shift provides cells with effective protection against cytotoxic radiation or chemotherapy, coupling the metabolic pathway to cellular resistance. This pathway has been shown to be totally independent of the tumor suppressor pathway of p53 and does not affect the tumor suppressor function of p53. This protective effect is selective to normal tissues, as it requires functional p53. Though not every cancer cell has detectable p53 mutation, essentially every cancer cell has dysfunctional p53. Therefore, cancer cells will not be protected by this strategy. Through a recently completed clinical trial, we have found that arsenic trioxide at 0.005 mg/kg administered intravenously (IV) for 3 days temporarily and reversibly suppresses p53 activation as measured in the peripheral lymphocytes of patients as a surrogate marker. We have also demonstrated that patients whose p53 activation was suppressed by this pretreatment with LDA had better blood counts during myelosuppressive chemotherapy compared to those whose p53 was activated.

Figure 2:
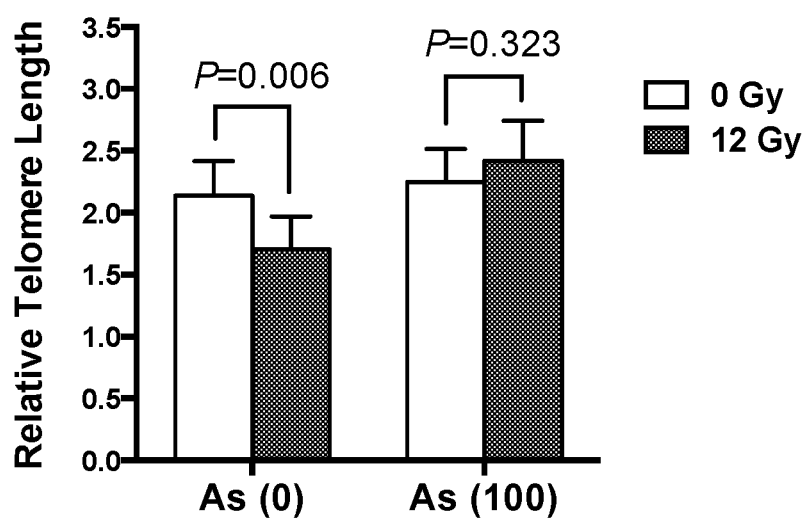
FIG. 2. T-lymphocytes isolated from healthy donors' peripheral blood were incubated with 10 µg/ml of Concanavalin A overnight. The cells were treated with either solvent or 100 nM arsenic (As) trioxide for 24 hours, followed by 12 Gy of X-ray treatment. Forty-eight hours later, the cells were harvested for telomere length measurement. The results represent four independent experiments. Paired student's t-test was used to calculate the p values.
Figure 3:
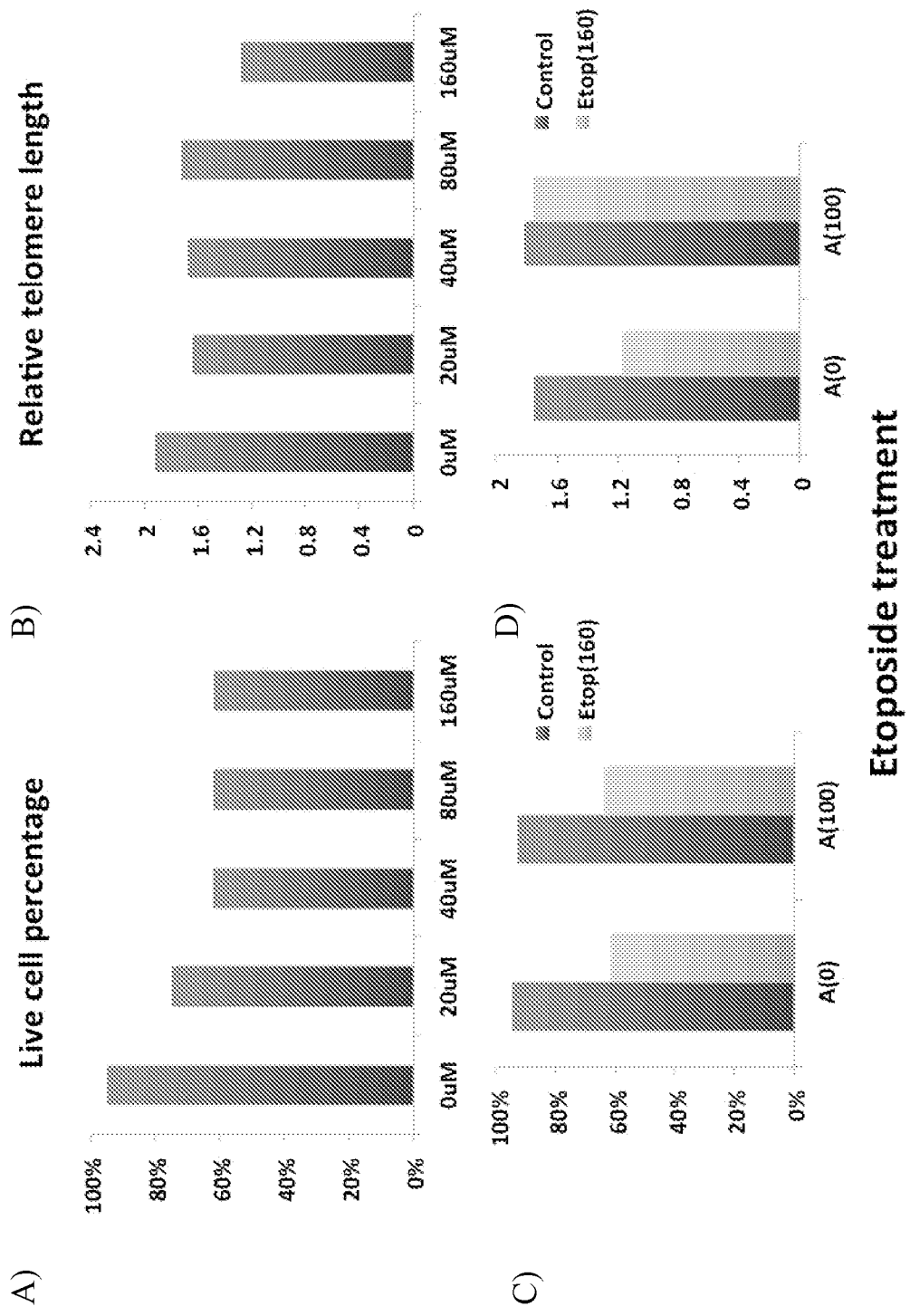
FIG. 3. (A) Live cell percentage and (B) relative telomere length of T-lymphocytes in response to a serial dilution of etoposide. (C) Live cell percentage and (D) relative telomere length of T-lymphocytes treated with solvent or 160 µM etoposide in the presence or absence of LDA pretreatment.
Figure 4:
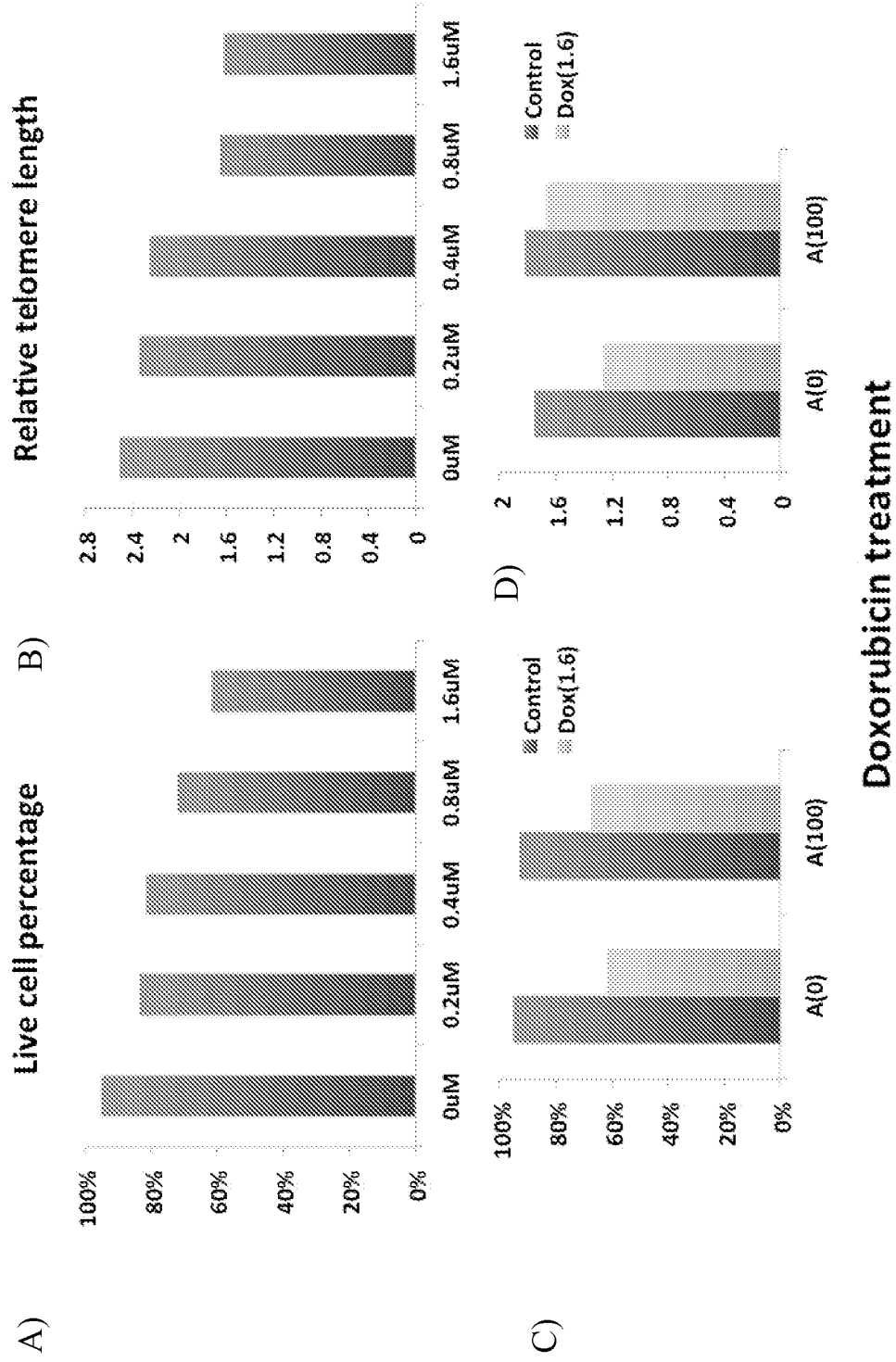
FIG. 4. (A) Live cell percentage and (B) relative telomere length of T-lymphocytes in response to a serial dilution of doxorubicin. (C) Live cell percentage and (D) relative telomere length of T-lymphocytes treated with solvent or 1.6 µM doxorubicin in the presence or absence of LDA pretreatment.
Figure 5:
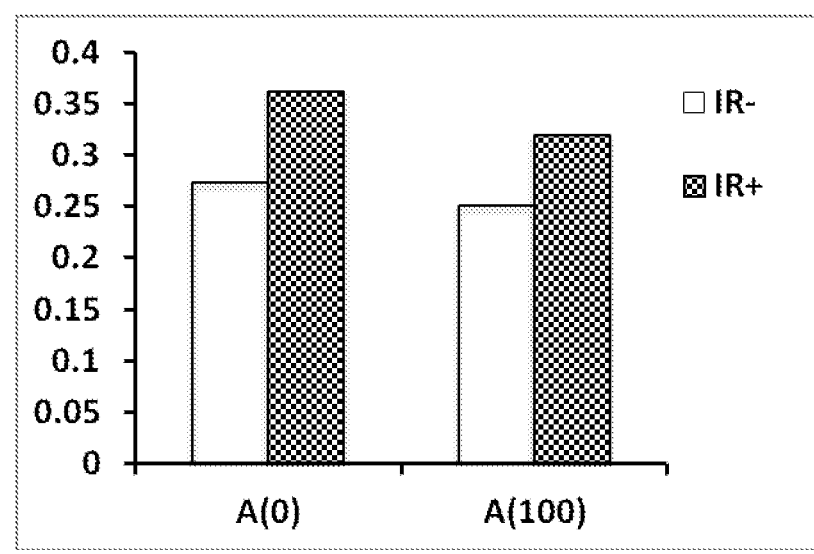
FIG. 5. Relative telomere length of T-cell leukemic cell line (Loucy) after 12 Gy of radiation in the presence or absence of LDA treatment.

Our in vivo data have demonstrated that LDA pretreatment protected bone marrow without compromising tumor response to Y-90 ibritumomab tiuxetan in a xenograft B-cell lymphoma model. LDA pretreatment also protected bone marrow cells from Y-90 ibritumomab tiuxetan induced loss of cellularity, DNA double strand break (DSB) and apoptosis (FIG. 1). Our recent in vitro data have demonstrated that LDA pretreatment of peripheral blood T-lymphocytes (obtained from donors' peripheral blood and proliferated with Concanavalin A) before radiation helps prevent shortening of telomere length (FIG. 2). Similar data have been also obtained with chemotherapy such as etoposide and doxorubicin in place of radiation (FIGS. 3 and 4). Of note, our data indicate that LDA does not make any difference in telomere length of leukemic cells, reassuring that our approach is selective toward non-malignant cells (FIG. 5).

As genomic instability caused by radiation or chemotherapy is attributable to the development of MDS, AML, and other therapy-related secondary malignancies, protection of the genome from these agents with LDA will help prevent or reduce the risk of the development of MDS, AML and other therapy-related secondary malignancies. LDA, used per our strategy, is the first agent we know of that has been demonstrated to protect the genome of normal cells from DNA damaging agents such as radiation and chemotherapy.

Another application of LDA may be in the treatment of diseases due to telomere dysfunction. The ability of LDA to protect the telomere in combination with its potential ability to activate telomerase activity may help overcome some of the consequences of telomere dysfunction that results in telomere syndromes such as dyskeratosis congenita.

Example 2

We have demonstrated in vitro that pretreatment with LDA at the concentration that temporarily and reversibly suppresses p53 activation helps maintain the telomere length after treatment or exposure to DNA damaging agents such as chemotherapy and radiation therapy. LDA, used per our strategy, is the first agent we know of that has been demonstrated to protect the genome of normal cells in these situations. This strategy may reduce the development of therapy (or exposure) related malignancy. Activation of a protein called p53 is a major pathway by which DNA-damaging agents cause normal tissue toxicity such as loss of hair, decrease in blood counts, nausea, vomiting and diarrhea. We have developed a novel strategy to temporarily and reversibly suppress p53 activation, thereby reducing normal tissue toxicity of treatment without compromising tumor control. This is achieved by a brief pretreatment with very low dose arsenic trioxide (LDA) prior to radiation or chemotherapy. This discovery was taken from our lab to a clinical trial that demonstrated proof-of-principle for our strategy. What we have discovered recently is that our strategy also protects DNA of bone marrow cells from damage by radiation in a mouse model. Our strategy has been also shown to protect telomeres, DNA-protein structures at the ends of chromosome that guard genomic integrity, from radiation and chemotherapy in an experimental model using human lymphocytes. We propose to investigate the mechanism behind protection of chromosomal DNA and telomeres from radiation by LDA, thereby protecting genomic integrity. We also propose to demonstrate our strategy reduces the incidence of a particular kind of DNA damage in bone marrow cells that leads to development of radiation-induced AML in a mouse model. We believe our research will lead to the first strategy to our knowledge that protects patients from therapy-related second cancers.

Secondary cancers such as myelodysplastic syndrome (MDS) and acute myeloid leukemia (AML) are major risks to life following primary cancer treatment in childhood. The development of these disorders has been attributed to genomic instability and the inability to repair DNA damage from ionizing radiation (IR) and chemotherapy in hematopoietic stem cells. There are data demonstrating that IR shortens the telomere length of human lymphocytes [obtained from donors' peripheral blood and proliferated with Concanavalin A (ConA)] and that bone marrow mononuclear cells undergo accelerated shortening of telomere length in patients treated with radioimmunotherapy such as Y-90 ibritumomab tiuxetan. Similar to IR exposure, radioimmunotherapy has been attributed to development of secondary MDS. Cancer survivors with shorter telomere length after the first cancer occurrence are more likely to develop a second malignancy. As telomeres are considered guardians of genomic stability, it is conceivable that the shortening of telomere length in hematopoietic cells of patients treated with IR could play a role in development of MDS. Mutations in genes that regulate DNA double strand break (DSB) repair have been also associated with an increased risk of secondary MDS and AML.

The present invention provides a novel strategy to protect the normal cells from DNA DSBs in vivo and prevent proliferating normal human lymphocytes from losing telomere length after IR in vitro. In the studies described herein, we will investigate the mechanisms underlying these findings with the goal, in one embodiment, of devising a new strategy, such as a small molecule approach, to reduce the incidence of therapy-related malignancies. We also propose to demonstrate the proof-of-principle that our strategy reduces chromosomal deletion associated with development of AML in a murine IR-induced AML model. Success of this in vivo study will set the stage for a large scale mouse study to test if our strategy can ultimately reduce the incidence of IR-induced AML.

Activation of p53 is one of major pathways by which DNA damaging agents such as IR and chemotherapy cause toxicity in normal tissues, inducing a cascade of events that eventually leads to cell senescence or cell death. We have reported that low dose arsenic (LDA), by temporarily and reversibly suppressing p53 activation at the time of treatment with IR or chemotherapy, reduces the normal tissue toxicity without compromising tumor response to treatment. Our in vitro and in vivo studies have shown that pretreatment of untransformed cells with LDA induces concerted p53 suppression and NF-kB activation, eliciting a marked induction of glycolysis. This metabolic shift provides cells with effective protection against cytotoxic IR or chemotherapy, coupling the metabolic pathway to cellular resistance. This pathway has been shown to be totally independent of tumor suppressor pathway of p53 and does not affect the tumor suppressor function of p53. Importantly, this protective effect is selective to normal tissues, as it requires functional p53. Though not every cancer cell has a detectable p53 mutation, essentially every cancer cell has dysfunctional p53. Therefore, cancer cells will not be protected by this strategy.

Arsenic has different biological effects in vitro and induces expression of different sets of genes depending on the dose. Our approach with LDA aims to mitigate certain known adverse biological effects. For example, arsenic trioxide is a cytotoxic agent used to treat acute promyelocytic leukemia (APL). However, the dose of arsenic trioxide used for our strategy is much lower than the dose used to treat APL. Arsenic is also a known carcinogen. However, epidemiological data suggest certain cumulative threshold doses are needed over a prolonged period for a carcinogenic effect. Of note, we have not observed any arsenic-induced malignancy in our animal model.

In addition to our in vitro and in vivo work with LDA in the setting of IR and chemotherapy as described herein, we have also developed a preclinical model to assess the efficacy of LDA as a cytoprotective agent from the bone marrow toxicity of radioimmuno- and radiopharmaceutical therapy using Y-90 ibritumomab tiuxetan as a model. To test the hypothesis that LDA protects bone marrow against Y-90 ibritumomab tiuxetan-induced damage, sex-matched BALB/c mice (4-6 weeks of age) were randomized into four groups: control, LDA only, Y-90 ibritumomab tiuxetan only, LDA pretreatment followed by Y-90 ibritumomab tiuxetan. LDA pretreatment was administered through drinking water containing 1 mg/L arsenic trioxide for three days. Y-90 ibritumomab tiuxetan was injected into mice at a dose of 200 µCi via tail vein. Tissue samples were collected at different time points (3 hours to 5 weeks) after treatment.

Bone marrow damage was analyzed histologically with hematoxylin and eosin (H&E) staining, DNA DSBs were assessed by γ-H2AX staining and apoptosis was detected by terminal deoxynucleotidyl transferase dUTP nick end labeling (TUNEL) staining. Y-90 ibritumomab tiuxetan treatments were associated with severe damage to bone marrow cells, as reflected by the loss of cellularity, and such bone marrow cell loss was significantly reduced by LDA pretreatment.

Consistent with this observation, γ-H2AX positive cells accumulated to a larger extent in mice treated with Y-90 ibritumomab tiuxetan from as early as 6 hours to a week after treatment, compared to mice pretreated with LDA. Remarkably, while DNA DSBs were considerably diminished in LDA-pretreated mice by 1 week after treatment, much greater damage was still observed in mice without LDA pretreatment. Similar data were obtained with TUNEL assay (FIG. 1).

To test the hypothesis that LDA does not protect malignant cells from IR, a mouse xenograft model was generated using a CD20 expressing lymphoma cell line, Karpas 422. Treatments were initiated 1 week after implantation when tumors became palpable. Tumor volumes were measured periodically with calipers. Tumor volume was calculated using the equation: volume=length×width×depth×0.5236 mm. Two independent experiments were done and the tumor volumes were expressed as means±SE. In this tumor xenograft model, the tumor volume of the control group continued to increase with time. LDA pretreatment did not have any detectable effect on the growth of the implanted tumors. As expected, treatment with a single dose of Y-90 ibritumomab tiuxetan resulted in marked tumor growth suppression. LDA pretreatment showed no effect on Y-90-induced tumor growth suppression.

As one of the first steps to explore the role of LDA in protecting the bone marrow from DNA DSBs as observed in FIG. 1 above, we studied the effect of LDA on telomere length in the setting of IR. We observed the expected shortening of telomere length in the peripheral T-lymphocytes (obtained from donors' peripheral blood and proliferated with ConA) after IR. However, pretreatment of these peripheral T-lymphocytes with LDA resulted in maintenance of telomere length after IR (FIG. 2).

Taken together, these data point toward the potential role of LDA in protecting the genome from IR, thereby protecting from development of secondary malignancy such as MDS. Additionally, data from a clinical trial supports a beneficial effect of LDA in patients. The trial had two objectives: 1) to define the lowest safe dose of arsenic trioxide that blocks p53 activation in patients and 2) to assess the potential of LDA in decreasing hematological toxicity from myelosuppressive chemotherapy. Patients scheduled for treatment with at least 4 cycles of myelosuppressive chemotherapy with a minimum of 2 weeks between the cycles were eligible. From the first stage of the study (first objective), we found that intravenous administration of arsenic trioxide at 0.005 mg/kg for 3 consecutive days suppresses p53 expression temporarily and reversibly for 4 to 5 days.

The p53 expression level in patients' peripheral lymphocytes was measured as a surrogate marker for p53 activity for the patients. None of these patients experienced any arsenic trioxide related toxicity. For the second stage of the study (second objective), patients were treated with chemotherapy without any LDA pretreatment before cycles 1, 3 and 5. They were treated with intravenous LDA of 0.005 mg/kg for 3 days prior to cycles 2, 4 and 6. We did not observe a clear period of p53 inactivation during the first few days of cycles 2, 4 and 6 as would have been expected from the in vivo model and from the first stage of the study. Because the competing and compounding effects of multi-drug chemotherapy on p53 were felt to affect the p53 activity even in the presence of LDA pretreatment, we decided to focus on p53 activity obtained just prior to chemotherapy administration (on day 1). If the p53 activity level for the subsequent cycle (e.g., cycle 2 for cycle 1, cycle 4 for cycle 3 etc.) was lower than the baseline cycle, p53 was defined as "suppressed" for the pair of cycles. If the p53 activity level for the subsequent cycle was higher than the baseline cycle, p53 was defined as "activated" for the pair of cycles. Repeated measures analyses of variation in absolute neutrophil counts (ANC), white blood cell (WBC), hemoglobin concentration (Hgb) and platelet counts were carried out for 26 patients. We assessed the significance of the association between categorical outcomes with Fisher's Exact test and demonstrated that the mean ANC, WBC, and Hgb were statistically significantly higher in the suppressed group relative to the activated group. Even with a relatively small sample size, we believe that we have generated very encouraging clinical data supporting the proof-of-principle that suppression of p53 could lead to protection of normal tissue-bone marrow in this particular study. These clinical data, in combination with in vitro and in vivo data presented so far, give us the impetus to expand our p53-based strategy from protection of normal tissues to protection of genomic integrity from DNA damaging agents, associated with development of AML in a murine IR-induced AML model.

Discovering the mechanism by which LDA protects genomic stability. We will use a nonbiased approach to discover the LDA-protective mechanism that utilizes a mutant mouse embryonic stem (ES) cell library representing the "montage" of genome maintenance genes (Table 1, abbreviations described in legend). A comprehensive library is needed since IR can induce radicals (indirect effects) that cause a variety of lesions including closely spaced strand breaks, abasic sites and oxidized bases and IR can directly cause DSBs. Thus, an ensemble of pathways is required to repair IR-induced lesions. Our library is used to identify pathways that correct 1,4-Benzoquinone (BQ)-induced DNA damage. BQ is a benzene metabolite implicated in the etiology of hematopoietic malignancies such as MDS/AML.

Discovering LDA essential genes that stabilize the genome. For these studies, we will use a comprehensive mouse ES cells library mutated for a variety of genome maintenance genes. For these studies, genome maintenance genes include those that repair DNA damage, stabilize replication forks and telomeres. A comprehensive library is provided in Table 1.

Important for this project is that our mutant ES cell library have a strong representation of genes in DNA DSB repair and replication fork maintenance pathways, as chemotherapeutics that lead to secondary MDS/AML cause DSBs, interstrand crosslinks and topoisomerase cleavage complexes. Furthermore, mutations in genes that regulate DSB repair and replication fork maintenance are associated with increased risk for hematopoietic cancers including secondary MDS/AML. In addition, high levels of environmental toxins that cause these double strand lesions, like benzene, correspond to elevated levels of MDS/AML. However, pathways that repair other forms of damage (single strand breaks, mismatches, indels, base lesions) will also be tested since they could contribute to the LDA protective effect.

For each mutant cell we will compare four groups exposed to 1) nothing, 2) IR but not LDA, 3) LDA but not IR, and 4) IR+LDA (abbreviated −/+IR −/+LDA). We will measure dose response/cell survival and DNA damage/mutation spectrum. We will look for mutations that negate LDA protection, thereby identifying LDA essential genes. A designation "LDA essential gene" will be given if the mutation impairs sodium arsenite-mediated amelioration to IR-induced toxicity.

To discover LDA essential genes, cell survival and DNA damage/mutation assays will be performed. First we will establish working doses for all control and mutant cells in Table 1 since they will vary depending on the mutation. As a pilot we started with ES cells mutated for Msh2 and p53 since mutations in both are implicated in the development and progression of secondary MDS/AML.

Figure 6:
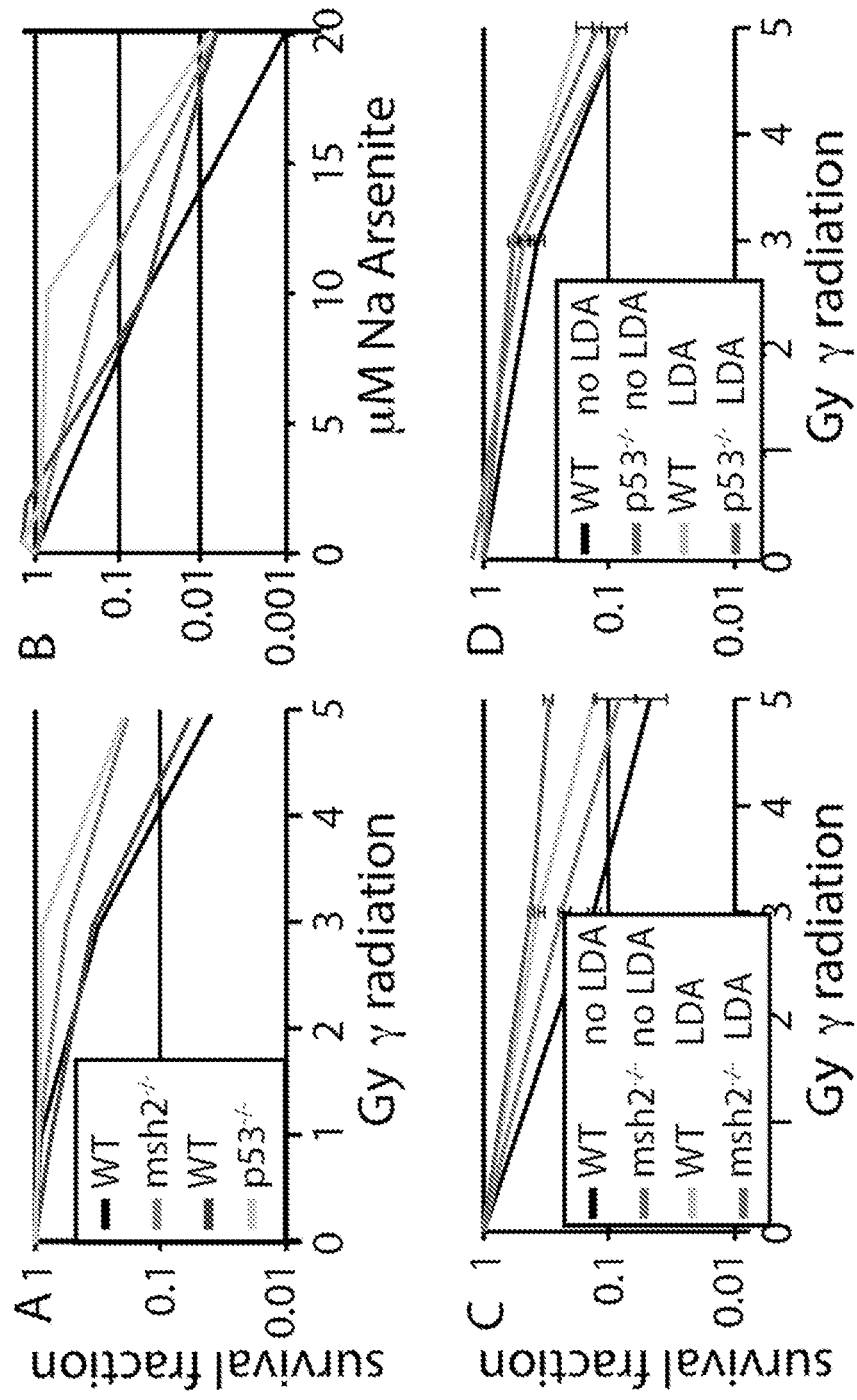
FIG. 6. Dose response to γ radiation and sodium (Na) arsenite. (A, B) Survival fraction curves to determine the working doses. The wild type (WT) cells (black, green) are the parental cells for the msh2 and p53 mutations, respectively. (C, D) Survival fraction curves with msh2−/− and p53−/− cells exposed to γ radiation and LDA (100 nM Na arsenite). Error bars are shown for the average of 3 independent experiments.

Msh2 is a member of mismatch repair (MMR) important for postreplication repair and homologous recombination regulation while p53 is essential for responses to a variety of stresses including DNA damage and ribosomal stress. Based on the dose response curve (FIGS. 6A, B), cells will be exposed to 100 nM sodium arsenite 24 hours before exposure to 3-6 Gy. From our first experiment we find that LDA protects both control and msh2$^{-/-}$ cells from γ radiation and the data suggest that Msh2 is not important for LDA-mediated protection to γ radiation (FIG. 6C). However, p53 appears to assist in LDA-mediated protection (FIG. 6D, note the p53-mutant lines are contained within the WT lines). Since the differences for the p5.3$^{-/-}$ cells and their control cells are small, we will repeat the experiment with different Na arsenite doses. If results are replicated, then we will conclude that p53 is an important contributor to LDA-mediated protection to γ radiation.

Next, we will measure genome damage/mutations using two assays. The first assay will detect mutations in the HPRT gene (resistance to 6-thioguanine). This is an unbiased approach to find a large assortment of genomic lesions ranging from point mutations and indels to chromosomal rearrangements. The second assay is two-color FISH on metaphase spreads that will detect chromosomal breaks, rearrangements and telomere loss using probes for the pericentromere and the telomere. The remaining experiments will be performed on only those cells that are mutated for LDA essential genes. Assays 2-5 described below test DSB repair and replication fork maintenance, assay 6 tests telomere health while assay 7 tests excision repair.

1. Validate the LDA essential genes. To ensure the designed mutation is the actual defect that causes the diminished response, we will express wild type cDNAs in the mutant cells that do not fully respond to LDA. In addition we will use a combination of shRNA and CRSPR/Cas9 to mutate the putative LDA essential gene in another strain of wild type ES cells and repeat the survival fraction and the mutation analyses.

2. Analyze the kinetics of DNA repair. To measure the repair of single strand gaps and DSBs, we will observe DNA damage foci (γH2AX, 53BP1, RAD51, FANCD2) 2, 6, 12 and 24 hours after −/+IR −/+LDA. More time points will be added if needed. This analysis will determine the time it takes for foci to form and dissipate. This is essential since IR causes DSBs and chemotherapeutics like topoisomerase inhibitors impede replication fork progression that could lead to mutations causing secondary MDS/AML.

3. Analyze unregulated recombination. We will measure sister chromatid exchanges (SCEs) and repeat fusion to determine if recombination is defective or unregulated. SCEs are recombination intermediates that form as a single strand invades and anneals to the sister chromatid. Repeat fusion (recombination between nonallelic inverted repeats) shows faulty template switching. An increase in SCEs and repeat fusion indicates unregulated homologous recombination or template switching that can lead to complex chromosomal rearrangements seen in a variety of cancers. Thus it is important to determine if LDA impacts the efficiency or regulation of homologous recombination/template switching after IR exposure in cells mutated for LDA essential genes.

4. Analyze DSB repair. We will test the repair of an I-SceI-induced DSB in a substrate specific for either homologous recombination (DR-GFP) or nonhomologous end joining between distal ends of two tandem DSBs (EJ5-GFP). Thus, the impact LDA has on the two major DSB repair pathways will be analyzed.

5. Analyze replication fork stability. We will use fiber analysis and iPOND (isolation of proteins on nascent strand) to measure the impact LDA has on IR-induced replication fork stalling, progression and nascent strand progression. These analyses will determine how LDA essential genes impact LDA's influence on replication fork stability after genotoxic exposure. Cells will be exposed to the replication fork blocker, hydroxyurea (HU) in addition to IR. Defective replication fork stability can lead to faulty replication and chromosomal breaks that can cause nonallelic recombination and complex rearrangements as we have previously shown.

6. Analyze telomere stability. We will measure telomerase activity and telomere length using the telomerase repeat amplification protocol (TRAP) assay and qPCR.

7. Analyze excision repair. We will apply a range of assays that measure the effectiveness of excision repair pathways. These assays test for short and long patch base excision repair, abasic site repair, glycosylase activity, PARP-1 activity (important for single strand and double strand break repair), polymerase β activity and AP endonuclease activity.

8. Epistatic analysis. It is possible that the genetic mutations will only partially diminish the LDA-mediated protective response (as appears to be the case for p53). Therefore, we will use shRNA and CRISPR/Cas9 to alter multiple genes in a single cell to determine if the genes are epistatic. If the genes appear to be in parallel pathways (a greater reduction in LDA protection than either single mutation), then we will also rescue the cells with wild type cDNAs to ensure we are not observing off-target affects.

Discovering p53's influence on the LDA protective effect. In our clinical trial, patients whose p53 was suppressed by LDA during myelosuppressive chemotherapy experienced a protective effect (higher mean ANC, WBC and Hgb) suggesting a decrease in apoptosis and cell senescence. LDA also reduced p53-mediated suppression of NF-kB to stimulate glycolysis (important for patient recovery).

We will evaluate the p53 response to IR-induced stress using p53$^{+/+}$ and p53$^{-/-}$ ES cells. Control and p53$^{-/-}$ cells, (−/+5Gy IR−/+1 µM LDA) will be tested for DNA damage, mutation spectrum, DSB repair and replication fork maintenance. In addition, we will measure the ATM (ataxia telangiectasia mutated) response to IR, since ATM phosphorylates p53 on serine 18 (pS18 in mice, pS15 in human) to stimulate p53 transcriptional activity. We will also diminish p53 activity with a lentivirus that expresses GSE22 (interferes with tetramerization) in cells mutated for LDA essential genes to test the role p53 plays in the LDA protective effect. The experiments proposed herein will be reproduced in these cells to establish the integration of p53-DDRs with LDA-mediated genome protection.

A comprehensive analysis of p53 function will be done by measuring the expression of p53-targets in control cells and cells mutated for LDA essential genes. For −/+IR−/+LDA cells, qRT-PCR will be used to measure transcription for p53 targets that induce: 1) proliferation arrest (p21), 2) apoptosis (BAX), 3) cell death (KILLER/DR5), 4) DNA repair (GADD45) and the negative feedback loop (MDM2) using conditions we have described. We will also evaluate p53-mediated regulation of glycolysis. p53 stimulates glycolysis by inducing transcription of hexokinase II, but suppresses glycolysis by reducing transcription of two glucose transporters (GLUT1 and GLUT4) and the insulin receptor. p53 also suppresses glycolysis by suppressing NF-kB induction of GLUT3 and by inducing transcription of TIGAR. We will measure the expression of these genes using qRT-PCR in −/+IR−/+LDA control cells and cells mutated for LDA essential genes.

Determining the mechanism by which LDA suppresses IR-induced telomere shortening. Telomeres are the specialized DNA-protein structures at chromosome ends that protect chromosome integrity by preventing end-to-end fusions, nucleolytic processing and homologous recombination. Telomeric DNA is comprised of tandem hexanucleotide repeats, with a length that is genetically determined and varies between individuals and cell populations. Telomere length shortens with aging in replicative tissues lacking the enzyme telomerase, a specialized reverse transcriptase that replenishes terminal telomeric repeats lost following genome duplication as a consequence of the 'end replication problem. Once a critically short telomere length is reached, telomeres lose their ability to protect telomere ends, triggering a DDR that results in cellular senescence or apoptosis. Thus, telomere length acts as a molecular clock for cellular replicative aging. This relationship extends beyond the cellular level, however, as telomere length is an independent and significant predictor of mortality, including risk of death from aging-related diseases in elderly individuals. Population-based studies have also demonstrated an inverse relationship between leukocyte telomere length and risk for primary cancers as well as other chronic health conditions characterizing elderly populations, such as dementia, pulmonary disorders, and cardiovascular disease.

Beyond genetic determinants of telomere length and the effects of aging, exposures to chemotherapy and IR contribute to accelerated rates of telomere attrition over time. Telomeres are hypersensitive to IR, leading to accelerated telomere shortening and damage to telomere ends. Cells may continue to divide despite this insult, permitting transmission of pre-malignant chromosomal aberrations to subsequent generations of cells thus increasing risk for malignant transformation. Therefore, in addition to association with risk for primary cancers, telomere shortening may also predict risk for therapy-related neoplasms. For example, lymphocyte telomere shortening precedes development of therapy-related AML and MDS in lymphoma patients who have undergone autologous bone marrow transplant. AML is also a feature of dyskeratosis congenita (DC), a syndrome resulting from mutations in genes that regulate telomere maintenance. Second cancers are the leading cause of non-relapse-related late mortality after childhood cancer, demonstrating a linear dose-response relationship relative to the degree of IR exposure. We have shown that in IR-exposed childhood cancer survivors, those with short telomeres are more likely to develop thyroid second malignant neoplasm (SMN). We are currently investigating the influence of genetic factors, such as regulators of telomere maintenance, upon risk for thyroid SMN. Early identification of survivors at increased risk for IR-related second cancers may permit interventions to reduce cancer risk and associated morbidities. However, at present there are no preventive strategies that attenuate biological effects of IR, specifically telomere shortening and dysfunction.

Hematopoiesis is particularly sensitive to shortened telomere length. For example, bone marrow failure is a highly penetrant phenotype of DC. In these individuals, bone marrow failure results from premature cellular senescence within the hematopoietic compartment, presumably secondary to pronounced telomere attrition. We have shown this impaired capacity for hematopoietic reconstitution to be recapitulated in a pediatric AML cohort receiving intensive chemotherapy, such that shorter remission telomere length predicts significant delays in recovery after later chemotherapy courses. Presently, there are no drugs incorporated into cancer treatment plans specifically to maintain telomere length following exposure to chemotherapeutics or IR. Our preliminary data suggest that IR-induced telomere attrition in T-lymphocytes may be mitigated by pre-treating cells with LDA (FIG. 2). Based on the relationship among accelerated telomere attrition, hematologic reconstitution and malignant transformation, LDA has significant potential impact for preventing both acute and late hematologic effects in individuals treated for cancer with chemotherapy and IR.

Androgen therapy was shown to mitigate rates of telomere attrition in a subset of individuals with telomere maintenance defects as measured over a 24 month period. Our preliminary data suggest LDA may prevent telomere attrition induced by IR over a period of days, a novel finding. Thus, compared to danazol, LDA holds the promise of aiding a different population of patients (those treated with IR), by affecting a different biologic phenomenon (attrition induced by IR rather than natural attrition). Given the short and long term effects of IR on hematopoiesis and the development of SMNs, this work will provide critical molecular understanding of the effect of LDA treatment on telomere length, and has potential to shift clinical practice paradigms.

Determining if LDA protects from IR-induced telomere shortening via effects on telomerase. Utilizing lymphocytes from healthy donors and from individuals with DC and other telomere biology disorders, we will investigate the impact of LDA upon telomere maintenance. We will first isolate T-lymphocytes from healthy donors' peripheral blood. Following stimulation with ConA, we will treat cells with either solvent [phosphate buffered saline (PBS)] or LDA for 24 hours, followed by 12 Gy IR. Forty-eight hours later, we will harvest cells for telomere length measurement. To determine if the suppression is conferred via a telomerase-dependent mechanism, at the time of treatment with either solvent or LDA, we will introduce the telomerase inhibitor BIBR1532 or solvent. We will confirm that telomerase has been inhibited at the time of IR treatment and at 48 hours post-IR using the TRAP assay (MilliporeSigma). Once inhibition is established, we will determine the effect of telomerase inhibition on telomere length after IR using quantitative real time PCR, a measure of telomeric content relative to a single copy locus, and Southern blotting, which allows for measurement of absolute telomere length.

Figure 7:
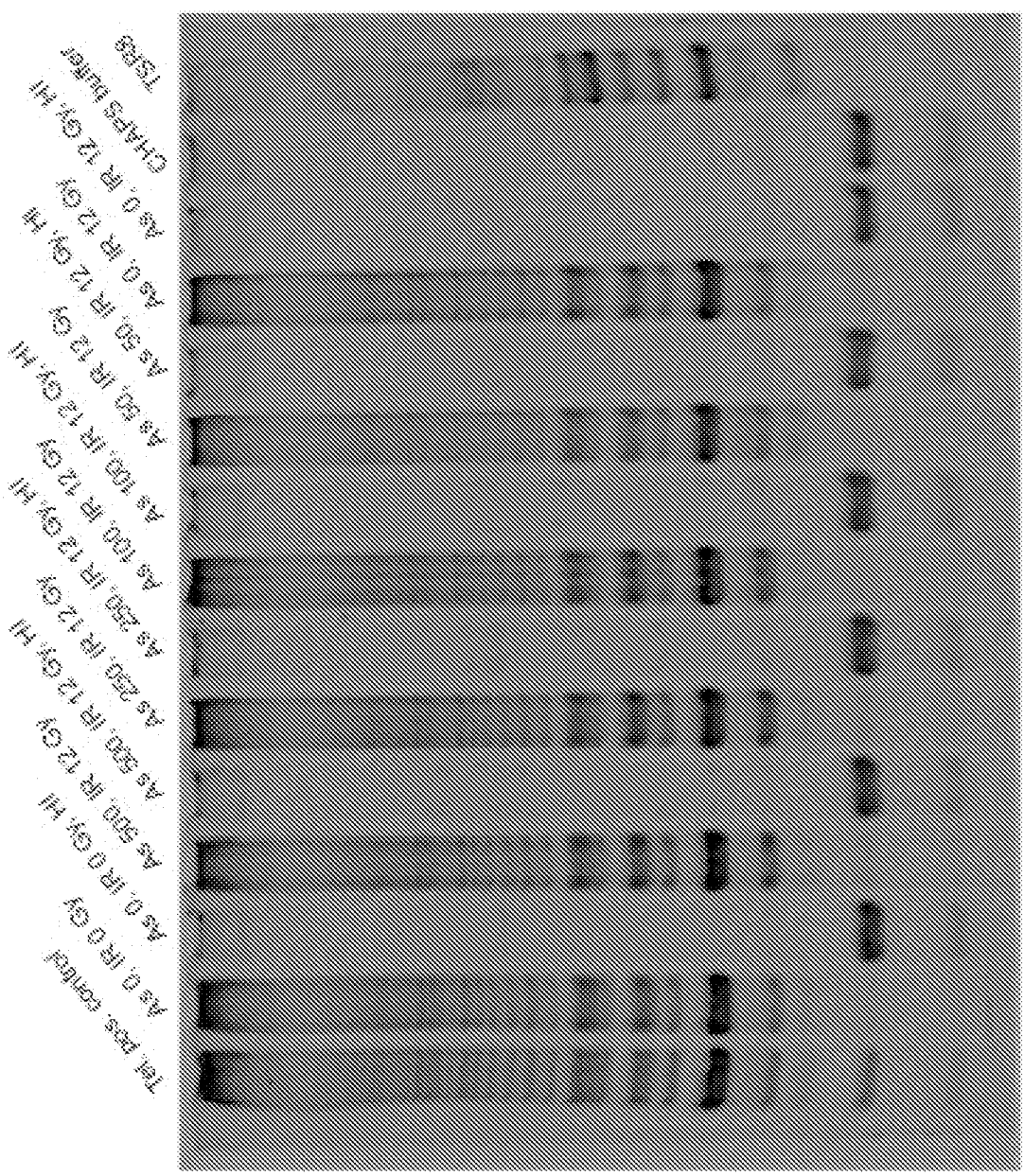
FIG. 7. HEK cells were stimulated with ConA, 10 µg/ml. After 24 hrs, LDA was introduced (range from 0 nM to 500 nM) and again incubated 24 hrs. 12 Gy of IR was delivered, cells were incubated an additional 48 hrs and harvested. Extracted protein (500 ng) was used to assess telomerase activity by TRAP, compared with a telomerase positive control and no-Arsenic, no-IR control. HI: heat inactivated.

In FIG. 7 we demonstrate that there is no obvious difference in telomerase activity, as measured by the TRAP assay, in response to IR or after varying degrees of exposure to arsenic in HEK 293T (SV40 transformed embryonic epithelial kidney cells). However, we will test this observation in T lymphocytes, which are known to dynamically regulate telomerase expression. This will better recapitulate the effect of LDA within the hematopoietic compartment.

If telomerase inhibition prevents LDA from suppressing telomere shortening following IR, we will next determine if this is the result of regulation of components of telomerase. Given telomeres shorten following IR without LDA pre-treatment (FIG. 2), it is possible that IR inhibits telomerase expression and this inhibition is prevented by LDA. To test these possibilities, we will examine the expression levels of telomerase holoenzyme components, TERT (catalytic subunit), hTR (RNA subunit), or dyskerin (required for biogenesis and stability). TERT and dyskerin levels will be determined by qPCR and western blotting and hTR levels by qPCR. If there are no changes in the levels of these core components, we will analyze the mRNA and protein levels of TPP1 and POT1, components of the shelterin complex that influence telomerase recruitment to telomeres and its ability to catalyze the addition of multiple telomere repeats upon a single binding event (a property known as repeat addition processivity), via qPCR and western blotting, respectively. We will assess whether there are effects on repeat addition processivity with a direct primer extension assay, as previously shown.

Determining if LDA protects from IR-induced telomere shortening via effects on telomere end protection We will test whether telomere end protection is altered following IR and if LDA prevents any observed effects. First, we will examine whether IR induces a DNA damage response at telomeres. A DNA damage response at telomeres is typically measured by the appearance of telomere dysfunction induced foci (TIF), foci of co-localized telomeric protein (e.g., TRF1 or TRF2) and DNA damage signaling protein (e.g., 53BP1 or γ-H2AX) visualized by immunofluorescence. Therefore, we will determine if there is an increase in TIFs in ConA stimulated T lymphocytes post-IR and at various points in time: 2, 6, 12, 24, and 48 hours following IR. Then, we will determine whether the number of TIFs or the kinetics of their appearance or disappearance changes with pre-LDA treatment as compared to treatment with solvent.

Next we will examine the effects of IR, with and without LDA pre-treatment, upon the association of factors mediating telomere end protection and telomere processing with telomeres. These include shelterin proteins TRF1, TRF2, TIN2, TPP1 and POT1; telomere processing factors, Apollo and SLX4; and the Ku heterodimer, comprised of Ku70 and Ku80. We will measure the telomere association of these proteins via chromatin immunoprecipitation (ChIP) assays, compared to Alu repeat association.

Finally, we will determine if IR induces changes in telomere 5' end resection, and if so, if LDA protects against this effect. To do this, we will perform telomere overhang assays, which will determine whether there are single stranded G-rich 3' or C-rich 5' overhangs at chromosome ends. This is accomplished by comparing hybridization of a probe specific for the G-rich strand or C-rich strand to native DNA vs. denatured DNA and in an *E. coli* exonuclease 1-dependent fashion. If IR induces an increase in the 3' overhang, we will determine if this increase is suppressed by LDA. Telomere 5' end resection is normally controlled by TRF2 repressing ATM signaling and CtIP/MRN-mediated resection and TPP1-POT1 repressing ATR signaling and Exol/BLM-mediated resection. In conjunction with the above studies assessing TRF2 and TPP1-POT1 at the telomere, we will determine if ATM and ATR are associated with telomeres in an IR-dependent fashion, and if this relationship is antagonized by LDA.

Determining if LDA promotes telomere lengthening in cells with compromised telomere or DNA repair due to germline defects. The ability of LDA to protect telomeres following IR raises the possibility that it might similarly improve telomeres under conditions of endogenous damage. Fanconi anemia and DC are inherited bone marrow failure and cancer predisposition disorders that are due to defective DNA intrastrand crosslink repair and telomere maintenance, respectively. Androgens may improve hematopoiesis in these patients, with some evidence to suggest that this effect is due to increased telomerase expression. Furthermore, androgen therapy (danazol) was recently shown to significantly reduce telomere attrition in individuals with telomere maintenance disorders. Therefore, we will determine the effect of LDA, compared with danazol, on telomerase activity and telomere length in T-lymphocytes isolated from individuals with these disorders compared with their healthy relatives. We will analyze biologic specimens obtained for pre-hematopoietic stem cell transplantation from over 20 subjects with DC and Fanconi anemia as well as healthy, unaffected parents. Telomerase activity and telomere length will be measured using the TRAP assay and qPCR, respectively. Subjects with DC include those with TERT, PARN, and TINF2 mutations. While the TERT and PARN mutations result in decreased telomerase activity, the mechanism by which the TINF2 mutations cause telomere shortening remains poorly defined. Therefore, we will test cells obtained from subjects with each of these mutation types to determine if LDA is effective in all or just a subset of defective cells. If an effect is observed with LDA, we will compare the efficacy to that of danazol and whether there are synergistic effects.

Accordingly, another application for LDA may be in the treatment of disease due to telomere dysfunction such as dyskeratosis congenita, given its ability to protect the telomere in combination with its potential ability to activate telomerase activity.

Quantifying LDA's contribution in maintaining genomic integrity in vivo using a surrogate assay for IR-induced AML (rAML).

While the mechanistic study for protection of genomic integrity by LDA is performed in vitro, this in vivo model will test the translational potential of our strategy in clinic. We will use CBA/Ca mice, a well-established murine model of IR-induced leukemogenesis. CBA mice irradiated with a maximal leukemogenic dose of 3 Gy have a 15% to 25% incidence of rAML, with the first leukemias occurring just under a year post-IR. The background AML incidence in unirradiated CBA mice is essentially zero. About 95% of rAML have a large, cytogenetically detectable deletion on chromosome 2 encompassing the PU.1 gene. This deletion is believed to be a crucial AML initiating step in mouse models. Bone marrow cells harboring chromosome 2 deletions are evident 24 hours post-IR. In strains of mice that are resistant to rAML, bone marrow cells with chromosome 2 deletions decrease to near background levels within a month. However, in rAML susceptible strains, cells with chromosome 2 deletions persist to at least 1 year post-irradiation. In this study, we will use the persistence of chromosome 2 deletion bearing bone marrow cells and their progeny in irradiated CBA mice as a surrogate for leukemogenesis and determine if LDA pretreatment reduces their frequency.

The experimental groups will be: 1. LDA+radiation, 2. PBS+sham radiation, 3. PBS+radiation, and 4.LDA+sham radiation. Eight week old CBA/Ca male mice will be used. Mice in groups 1 and 4 will be treated on three consecutive days with intraperitoneal injections of LDA. Mice in groups 2 and 3 will be injected with PBS instead. One day after the last injection, the mice will be irradiated, unanesthetized, to the whole body with 3 Gy of γ-ray at a dose rate of about 1 Gy/min using Cs irradiator (J. L. Shepherd Model 81-14A).

At 7, 30, and 180 days post-irradiation, bone marrow cells will be harvested from 10 mice of each group and metaphase spreads prepared. Chromosome 2 deletions encompassing the PU.1 gene will be detected by fluorescence in situ hybridization (FISH). Two PinPoint™ FISH probes, one detecting PU.1 and labeled with Cy3, and the other detecting a sequence well proximal to deletions observed in murine AML and labeled with fluorescein, will be constructed. Hybridization, acquisition of images and scoring of deletions will be done. Four hundred to five hundred metaphases will be scored for each mouse per the sample size calculation below. We anticipate the irradiated mice pretreated with LDA (group 1) have fewer bone marrow cells with chromosome 2 deletions than irradiated mice not pretreated (group 3). Groups 2 and 4 are controls to determine the background level of spontaneous chromosome 2 deletions (historically less than 1%) and the effect of the LDA treatment alone.

Sample Size: Data demonstrated that 4 CBA mice receiving 3 Gy at baseline had 167 of 2035 metaphases [mean=0.082 (=167/2035)] exhibiting PU.1 deletions at 30 days. Assuming a balanced design, N metaphases per group (groups 1 and 3), and the number of metaphases exhibiting PU.1 deletions following Poisson distributions with mean $\lambda_1$ and $\lambda_3$ in the group 1 and group 3 respectively, a sample size of N=3900 metaphases per group will achieve 90% power for testing $H_o$: $\lambda_1 = \lambda_3$ versus $H_o$: $\lambda_1 < \lambda_3$ if $k_3 = 0.082$ and $\lambda_1 = 0.066$, a 20% reduction in the mean with group 1 relative to group 3, with a significance level of 5% [PASS Version 11, NCSS Kaysville Utah 2011]. We plan to count 400-500 metaphases from each mouse and there will be 10 mice per group. With this design, we will observe approximately 4,000 (=10×400) to 5,000 (=10×500) metaphases at 30 days post-treatment in groups 1 and 3. If the assumptions of the power calculation ($\lambda_1 = 0.066$, $\lambda_3 = 0.082$) are correct, then this study will attain 90% power for testing the null hypothesis $H_o$.

Analysis: Metaphase counts and PU.1 deletions will be summarized by treatment group and time point. Treatment groups will be contrasted with regard to the mean using a generalized estimating equations model with distribution=Poisson and link=log. All statistical testing will be conducted with a 5% level of significance. SAS Version 9.4 for Windows [SAS Institute, Cary, N.C.] will be used throughout.

Example 3

We performed a loss of heterozygosity (LOH) assay to detect mutations in the HPRT gene [resistance to 6-TG (thioguanine)] utilizing a mouse embryonic stem cells that express RAD51$^{K133A}$. We used a knockout-knockin strategy that introduces RAD51$^{K133A}$ adjacent to the mouse RAD51 promoter while restoring miniHPRT, a positive/negative selection cassette: select for expression in HAT (hypoxanthine, aminopterin, thymidine) and select against expression in 6-TG. We screen for LOH of miniHPRT by selecting in 6-TG. Using this assay, we can detect a broad range of mutations. RAD51 is a recombinase that is essential for DNA double strand break repair and for protecting the nascent strand during replication. The K133A mutation is in the highly conserved Walker A motif and it causes a defect in ATP binding that disables the ability of RAD51 to induce topological changes in duplex DNA in an ATP-dependent manner.

Figure 8:
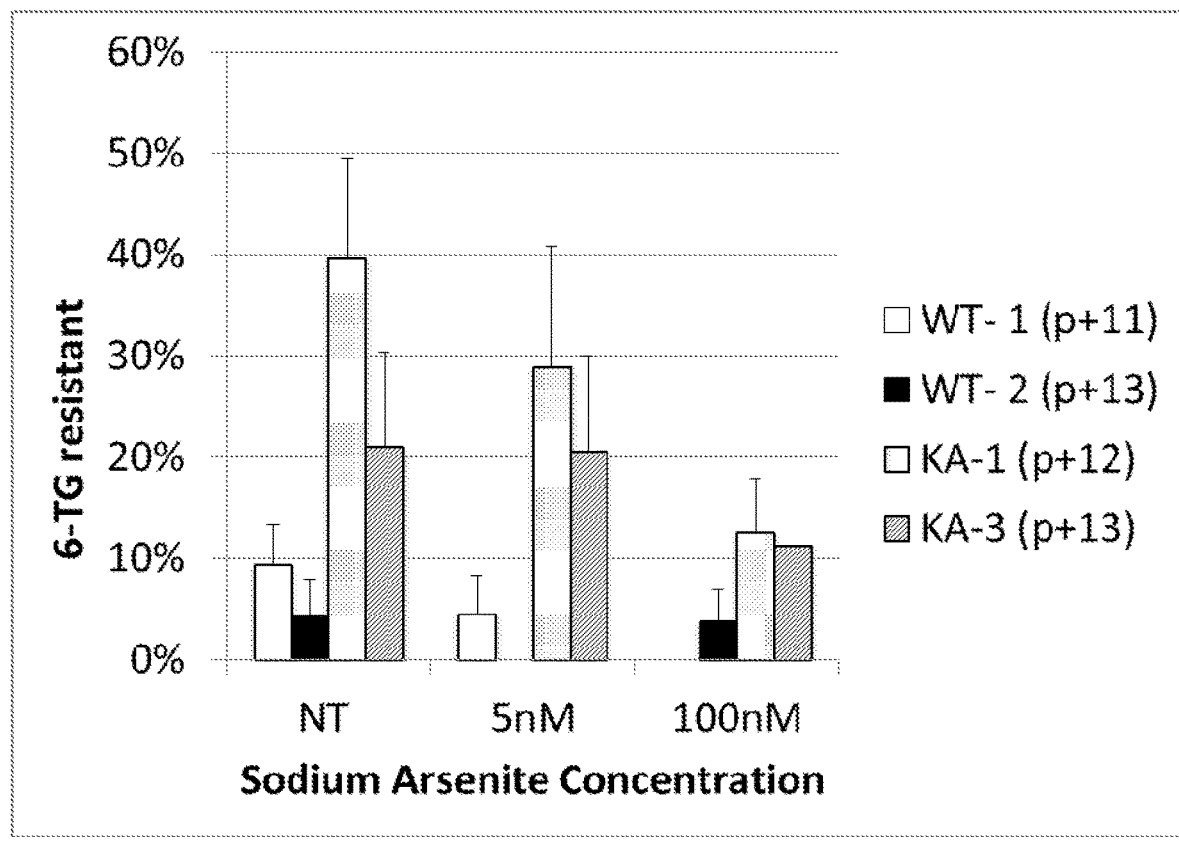
FIG. 8. Analysis of loss of heterozygosity assay in mutant embryonic stem cells expressing RAD51$^{K133A}$, KA-1 and KA-3, reveals enhanced spontaneous deletion of miniHPRT but addition of sodium arsenite 5 nM and 100 nM reduces the deletion as manifested by the proportion of surviving cells in 6-TG. NT; no arsenite treatment, WT; wild type embryonic stem cells, KA; mutant embryonic stem cells expressing RAD51$^{K133A}$ While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

For this assay, mutant mouse embryonic stem cells expressing RAD51$^{K133A}$ were passaged two times while being selected in HAT to remove any cells that spontaneously deleted miniHPRT. Then LDA and HAT were applied to these cells for 2 days. Cells were kept in fresh LDA and HAT for 3 more days. Next, cells were in fresh media containing LDA only for 1 day. Cells were then seeded onto new plates in 6-TG and colonies were counted 8 days later. Cells were also seeded without 6-TG as a control for seeding efficiency and to ensure that LDA was not toxic to cells. Shown in FIG. 8 is the percentage of 6-TG-resistant cells normalized to the no 6-TG control. It shows LDA reduced the level of deleting miniHPRT located on chromosome 2 in cells that expressed RAD51$^{K133A}$. Expression of RAD51$^{K133A}$ enhanced the spontaneous deletion of miniHPRT located on chromosome 2 but addition of 5 nM or 100 nM sodium arsenite reduced this deletion.

In this patent application, all U.S. patents, U.S. patent applications, and other non-patent documents are incorporated by reference herein. The text of such U.S. patents, U.S. patent applications, and other materials is however only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

TABLE 1

Mutant ES cell library

| Controls | Mutants | Mutations | Function |
| --- | --- | --- | --- |
| AB1.1 | Msh2 | −/− | MMR |
| AB2.2 | Brca2 | exon 27 del | HR |
| | Blm | 88% decrease | helicase/HR |
| | Recq15 | −/− | helicase/HR |
| | Trex2 | −/− | exonuclease/RF |
| | Fancb | exon 2 del | ICLR/RF |
| | Rad51K133A | DN | HR |
| | Rad51K133R | DN | HR |
| | Top3β | +/− | topoisomerase |
| | Top3α | +/− | topoisomerase |
| B44 | Xpa | −/− | NER |
| | Xpc | −/− | NER |
| J1 | Ku70 | −/− | cNHEJ |
| TC1 | H2AX | −/− | DDR/HR |
| | Cer | −/− | cNHEJ |
| | Brca1 | BRCT del | DDR/HR/NHEJ |
| | Sirt1 | −/− | HDAC |
| IB10 | Rad18 | −/− | lesion bypass |
| E14 (IB10) | Rad52 | −/− | HR |
| | Rad54 | −/− | HR |
| | Mus81 | −/− | endonuclease/HR |

TABLE 1-continued

Mutant ES cell library

| Controls | Mutants | Mutations | Function |
|---|---|---|---|
| | Ercc1 | –/– | NER/HR/ICLR |
| | Rev1 | BRCT del | TLS |
| R1 | RTEL1 | –/– | HR/telomere |

–/–, homozygote mutant,
+/–, heterozygote mutant.
Del, deletion.
DN, dominant negative.
MMR, mismatch repair.
HR, homologous recombination.
RF, replication fork.
NER, nucleotide excision repair.
cNHEJ, classical nonhomologous end joining.
DDR, DNA damage response.
HDAC, histone deacetylase,
ICR, interstrand crosslink repair.
TLS, translesion synthesis.

What is claimed is:

1. A method of reducing the risk of developing a secondary malignancy in a subject undergoing radiation treatment and/or chemotherapeutic treatment of cancer cells present in the subject, comprising:
    a) administering to the subject one or more compounds of arsenic in a protective amount of from about 1 μg/kg/day to about 125 μg/kg/day, wherein the one or more compounds of arsenic are administered to the subject at least one day prior to administration of radiation and/or one or more chemotherapeutic agents to the subject, and wherein the one or more of the compounds of arsenic are administered to the subject intravenously; and
    b) administering to the subject radiation and/or one or more chemotherapeutic agents subsequent to administration of the one or more of the compounds of arsenic.

2. The method of claim 1, wherein the one or more compounds of arsenic comprise arsenic trioxide.

3. The method of claim 1, wherein the protective amount of the one or more compounds of arsenic is from 1 μg/kg/day to 30 μg/kg/day.

4. The method of claim 1, wherein the one or more compounds of arsenic are administered to the subject at least three days prior to administration of radiation and/or one or more chemotherapeutic agents to the subject.

5. The method of claim 1, wherein the one or more compounds of arsenic are administered to the subject for at least three consecutive days prior to administration of radiation and/or one or more therapeutic agents to the subject.

6. The method of claim 1, wherein the subject is a pediatric subject.

* * * * *

UNITED STATES PATENT AND TRADEMARK OFFICE
CERTIFICATE OF CORRECTION

| | | |
|---|---|---|
| PATENT NO. | : 10,842,814 B2 | Page 1 of 1 |
| APPLICATION NO. | : 16/326049 | |
| DATED | : November 24, 2020 | |
| INVENTOR(S) | : Ha et al. | |

It is certified that error appears in the above-identified patent and that said Letters Patent is hereby corrected as shown below:

In the Specification

Column 15, Line 7: Please insert a paragraph break between "malignancy." and "Activation"

Column 25, Line 18: Please correct "$k_3$" to read -- $\lambda_3$ --

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*